(12) United States Patent
Meter

(10) Patent No.: US 11,980,167 B2
(45) Date of Patent: May 14, 2024

(54) METHOD FOR SAMPLING AN EGG

(71) Applicant: SELEGGT GmbH, Cologne (DE)

(72) Inventor: Tjitze Meter, Veenendaal (NL)

(73) Assignee: SELEGGT GmbH, Cologne (DE)

( * ) Notice: Subject to any disclaimer, the term of this patent is extended or adjusted under 35 U.S.C. 154(b) by 925 days.

(21) Appl. No.: 16/966,019

(22) PCT Filed: Feb. 7, 2018

(86) PCT No.: PCT/EP2018/053094
§ 371 (c)(1),
(2) Date: Jul. 30, 2020

(87) PCT Pub. No.: WO2019/154493
PCT Pub. Date: Aug. 15, 2019

(65) Prior Publication Data
US 2020/0359606 A1    Nov. 19, 2020

(51) Int. Cl.
| | | |
|---|---|---|
| *A01K 45/00* | (2006.01) | |
| *A61L 2/00* | (2006.01) | |
| *B23K 26/359* | (2014.01) | |
| *B23K 26/38* | (2014.01) | |
| *B23K 26/402* | (2014.01) | |
| *G01N 1/14* | (2006.01) | |
| *G01N 33/08* | (2006.01) | |

(52) U.S. Cl.
CPC .......... *A01K 45/007* (2013.01); *A61L 2/0029* (2013.01); *B23K 26/359* (2015.10); *B23K 26/38* (2013.01); *B23K 26/402* (2013.01); *G01N 1/14* (2013.01); *G01N 33/08* (2013.01); *G01N 2001/1445* (2013.01)

(58) Field of Classification Search
CPC ...... A01K 45/007; A01K 43/00; A01K 43/04; A61L 2/0029
See application file for complete search history.

(56) References Cited

U.S. PATENT DOCUMENTS

| | | |
|---|---|---|
| 5,699,751 A | 12/1997 | Phelps et al. |
| 6,286,455 B1 | 9/2001 | Williams |
| 9,686,969 B2 | 6/2017 | Meissner et al. |

(Continued)

FOREIGN PATENT DOCUMENTS

| | | |
|---|---|---|
| WO | 00/22921 A1 | 4/2000 |
| WO | 2017/204636 A2 | 11/2017 |
| WO | 2018/023105 A1 | 2/2018 |

OTHER PUBLICATIONS

Vision Systems Design;Food & Beverage: Vision system speeds egg crack detection, Dec. 1, 2009; https://www.vision-systems.com/articles/print/volume-14/issue-12/departments/techno . . . .

*Primary Examiner* — Yvonne R Abbott-Lewis
(74) *Attorney, Agent, or Firm* — N.V. Nederlandsch Octrooibureau

(57) ABSTRACT

The present invention relates to a method for sampling an egg, the method comprising;
a) fluid coupling an interior of the egg to a source of pressure,
b) controlling the pressure in the interior of the egg by the source of pressure,
c) expelling an amount of fluid, in particular allantoic fluid, from the interior of the egg to the exterior of the egg as a result of the pressure in the interior of the egg, and
d) collecting at least a portion of the amount of fluid at the exterior surface of the egg.

20 Claims, 9 Drawing Sheets

(56) References Cited

U.S. PATENT DOCUMENTS

| | | | | |
|---|---|---|---|---|
| 9,861,082 B2* | 1/2018 | Smaal | ............... | A01K 43/00 |
| 11,596,130 B2* | 3/2023 | Einspanier | ........... | A01K 45/007 |
| 2006/0075973 A1* | 4/2006 | Wolfe | ................. | A01K 45/007 |
| | | | | 119/6.8 |
| 2008/0289578 A1* | 11/2008 | Rybarczyk, Jr. | ........ | G01N 33/08 |
| | | | | 119/6.8 |
| 2010/0307419 A1* | 12/2010 | Nadreau | .............. | A01K 45/007 |
| | | | | 119/6.8 |
| 2015/0136030 A1 | 5/2015 | Meissner et al. | | |

* cited by examiner

METHOD FOR SAMPLING AN EGG

FIELD OF THE INVENTION

The present invention relates to a method for sampling an egg, in particular to sampling an egg in order to determine the gender of an embryo in the egg.

BACKGROUND ART

Determining the gender of the chicken embryo in the egg based on the presence of a gender specific compound in the allantoic fluid sample, is known per se. For example, WO9814781A1 relates to a method of determining the gender of a bird in ovo and comprises detecting the presence or absence of an elevated level of a sex-related hormone in the allantoic fluid of the bird egg, and then determining the gender of the bird within the egg from the presence of an elevated level of a sex-related hormone therein. The sex-related hormone is an estrogen. The method is carried out on chicken eggs between set and hatch.

Known methods of determining the gender of birds in ovo are considered too slow, are too impractical and/or too unreliable for industrializing purposes, and do cause too much loss. In particular, methods, of determining the gender of birds in ovo, that involve entry of a needle into the interior of an egg results in a risk of pollution and loss of the embryo.

SUMMARY OF THE INVENTION

The object of the invention is to improve a method of determining the gender of birds in ovo in that the risk of polluting the interior of an egg that is subject of the method, is reduced.

A further object of the invention is to improve a method of determining the gender of birds in ovo in that a problem with known methods is at least partly solved.

Another object of the invention is provide an alternative method of determining the gender of birds in ovo.

The invention therefore provides a method for sampling an egg, the method comprising;

a) fluid coupling an interior of the egg to a source of pressure,
b) controlling the pressure in the interior of the egg by the source of pressure,
c) expelling an amount of fluid, in particular allantoic fluid, from the interior of the egg to the exterior of the egg as a result of the pressure in the interior of the egg, and
d) collecting at least a portion of the amount of fluid at the exterior surface of the egg.

Coupling an interior of the egg to a source of pressure enables to prevent ingress of pollution into the interior of the egg. Fluid coupling an interior of the egg to a source of pressure without making a hole in the shell of the egg even more prevents ingress of pollution into the interior of the egg.

The source of pressures is able to apply any suitable pressure to the interior of the egg, like overpressure or underpressure compared to pressure at the exterior of the egg which is normally the standard atmospheric pressure.

The fluid in "fluid coupling" may be a gaseous fluid or a liquid fluid or a combination thereof. For example fluid coupling to an air cell of the egg is a gaseous coupling between air in the cup and air in the air cell. The air cell of an egg functions as an expansion vessel for the egg. Therefore, the air cell membrane is flexible.

Controlling the pressure in the interior of the egg by the source of pressure may involve one or more of maintaining a constant pressure in time, varying the pressure in time, and periodically varying the pressure in time. Controlling the pressure in the interior of the egg may involve controlling the pressure in any suitable compartment in the egg like in particular the air cell, however the albumin and allantoic cavity are e.g. also conceivable. An egg is compartmentalized and the compartments are defined by the egg shell and membranes, like the air cell by the air cell membrane. The object of controlling the pressure in the interior of the egg by the source of pressure is expelling an amount of fluid from the interior of the egg to the exterior of the egg.

It will be clear that sampling here means gathering of matter from the egg to aid in the process of a diagnosis and/or evaluation of for example the gender of a chicken embryo.

It has been found that, as a result of applying an overpressure in the interior of the egg, an amount of allantoic fluid is expelled at a sampling position from the interior of the egg to the exterior of the egg. This is possible because of the porosity of the egg shell. The egg shell adjacent the air cell has a porosity that enables to apply an overpressure to the interior of the egg through the air cell.

The expelling of the amount of allantoic fluid at the sampling position can be further improved by applying suction at the sampling position.

The sampling position is at the allantoic cavity, also allantois. The sampling position is past the air cell membrane, as seen from the air cell.

In an embodiment, the method further comprises determining a sampling position at the exterior surface of the egg; and step d) comprises collecting the portion of the amount of fluid at the sampling position. This facilitates the collecting of the portion of the amount of fluid at the exterior surface of the egg. Determining the sample position may involve any suitable way of sensing the egg, like imaging, thermo-imaging, measuring shell thicknesses. The image data can for example be used to avoid damage to the air cell, a blood vessel etc. In general the sampling position is at the egg shell between the air cell and the centre of the egg.

In an embodiment, the method further comprises making a sample passage in an egg shell for fluid communication between an interior of the egg and an exterior of the egg; and step d) comprises collecting the portion of the amount of fluid at the sample passage. The sample passage facilitates collecting the portion of the amount of fluid since expelling the amount of fluid to the exterior of the egg is easier as well as the sampling position is more predictable. The sample passage may have any suitable cross-sectional area. Preferably, the sample passage has a dimension, like a diameter, smaller than 1 mm, in particular smaller than 600 μm, like for example a diameter of about 100 μm. The smaller the cross-sectional area of the sample passage, the less chance of ingress of pollution into the interior of the egg.

In an embodiment of the method, the making a sample passage in an egg shell for fluid communication between an interior of the egg and an exterior of the egg comprises providing a number of passages, wherein the number of passages are preferably arranged in a pattern having a triangular shape, and wherein preferably the number of passages are arranged within a surface of 4 mm2 up to 100 mm2. The providing a number of passages makes the sampling method more redundant and more predictable in terms of expelled amount of fluid. The number of passages can also be arranged in a circular shape.

In an embodiment of the method, the sample passage has a tapered shape like a conical shape that tapers toward the exterior of the egg. This facilitates expelling the amount of fluid and prevents ingress of pollution.

In an embodiment of the method, the making the sample passage comprises one or more processing steps of laser processing, puncturing, cutting, milling and drilling. The laser processing is advantageous because it is a fast and flexible method that does not involve any member entering into the interior of the egg.

In an embodiment of the method, the making the sample passage comprises disinfecting the egg shell proximate the sample passage, wherein preferably the disinfecting comprises laser processing the egg shell proximate the sample passage. Disinfection the egg shell proximate the sample passage, even more prevents ingress of pollution into the interior of the egg. The disinfecting comprising laser processing easy combinable with the laser processing of the sample passage. It is also conceivable to mark the egg by laser processing, like adding an egg identification or any desired text or image to the egg shell. Preferably the same laser unit is used for making the sample passage, disinfecting and marking.

In an embodiment of the method, the fluid coupling an interior of the egg to a source of pressure comprises coupling the source of pressure to an air cell of the egg. The source of pressure can be coupled to any compartment within the egg, however the air cell is in particular suitable to fluid couple with because the permeability of the egg shell at the air cell is much better compared with the remainder of the egg shell. The source of pressure can be any suitable pump of pressure vessel. It is however conceivable to use a heat source like a microwave source to heat the egg or at least a portion of the egg. The increase of temperature increases the pressure in the interior of the egg.

In an embodiment of the method, the fluid coupling an interior of the egg to a source of pressure comprises making a flow path through the eggs shell to provide a pressure connection between the source of pressure and the interior of the egg. The flow path is an alternative to a number of parallel pores in the egg shell that technically form a flow path. The flow path made through the egg shell is however more predictable in terms of flow characteristics. Fluid coupling includes a gas coupling however a liquid coupling is conceivable as well.

In an embodiment of the method, making a sample passage and/or making a flow path comprises processing an outer egg shell and intermediate layers between the outer egg shell and the interior of the egg with different processing steps. Examples of such intermediate layers are; outer membrane, middle membrane, deeper membrane. Processed an outer egg shell and intermediate layers with different processing steps enables to optimize the permeability of the egg at the flow path and/or sample passage even more.

In an embodiment of the method, controlling the pressure in the interior of the egg by the source of pressure comprises applying a pressure difference between the interior and the exterior of the egg.

In an embodiment of the method, the pressure difference is variable over time and preferably the pressure difference is set at a neutral pressure for a neutral period of time and at an active pressure for an active period of time. The neutral pressure at the neutral stage ensures that there is no transport of air or liquid between the interior and the exterior of the egg. Overpressure during an active period of time is an outbound stage that enables transport from the interior to the exterior of the egg. Underpressure during an active period of time is an inbound stage that enables transport from the exterior to the interior of the egg.

In an embodiment of the method, the fluid coupling the interior of the egg to a source of pressure comprises engaging a contact area of the egg shell, preferably a contact area at the air cell. The contact area has a surface area that is suitable to cover a number of pores. Preferably the contact area extends over the entire air cell of an egg. This way, the fluid coupling involves substantially all of the pores at the air cell. The diameter of a pore is 1 to 10 micrometre. The egg shell can easily have 200 pores per square cm, and much more at the air cell since pore density is much higher at the air cell.

In an embodiment, the method further comprising sensing at least a portion of the egg to obtain sensor data and making the sample passage depending on the sensor data, in particular determine a position of the sample passage depending on the sensor data, wherein sensing the egg comprises at least one or more of imaging at least a portion of the egg and measuring a position of the egg. This will facilitate the expelling an amount of fluid from the interior of the egg to the exterior of the egg since the sample passage can be made in the vicinity to the targeted fluid like the allantoic fluid.

In an embodiment, the method further comprises arranging a fluid intake member at the sample position; and step d) comprises collecting the portion of the amount of fluid with the fluid intake member. The fluid intake member facilitates the collecting at least a portion of the amount of fluid at the exterior surface of the egg.

In an embodiment of the method, the fluid intake member is arranged on the exterior of the egg at least before the end of the incubation, like before start of incubation, and is used during incubation. The fluid intake member can be arranged on the exterior of the egg irrespective a sample passage is made at the sample position or not. Normally, the fluid intake member is arranged on the exterior of the egg at or before the egg is sampled.

In an embodiment of the method, the fluid intake member comprises an absorb organ and the taking in the portion of the amount of fluid is based on absorbency between the absorb organ and the portion of the amount of fluid. The absorb organ can be any suitable tissue paper or blotter paper. The absorb organ facilitates not only collecting the portion of the amount of fluid but also maintains the portion at the sample position.

In an embodiment of the method, the fluid intake member comprises a capillary tube and the taking in the portion of the amount of fluid is based on capillary action between the capillary tube and the portion of the amount of fluid.

In an embodiment, the method comprises pressurizing the interior of the egg for as long as the sample passage is open for fluid communication between the interior of the egg and the exterior of the egg. This even more prevents ingress of pollution into the interior of the egg.

In an embodiment, the method comprises monitoring the amount of expelled sample fluid to obtain sample fluid amount data and comparing the fluid amount data with a defined minimum amount data and depending on the step of comparing, repeating, intensifying or maintaining at least step c), or closing the sample passage. This assures control with respect to the amount of sample fluid. Intensifying may involve an increase of pressure applied. As an option it is conceivable that another sample passage is made to speed up step c). As a further option it is conceivable that another sample passage is made to retry or repeat step c).

In an embodiment, the method comprises closing the sample passage to stop fluid communication between the interior of the egg and the exterior of the egg. This even more prevents ingress of pollution into the interior of the egg.

In an embodiment of the method, the closing the sample passage comprises contacting the sample passage with a closure element and the method comprises depressurizing the interior of the egg after contacting the sample passage with the closure element in order to increase a closing contact between the closure element and the sample passage. The closure element even more prevents ingress of pollution into the interior of the egg. It is conceivable to apply underpressure to the interior of the egg to firmly suck the closure element in, against or to the sample passage.

In an embodiment of the method, the closing the sample passage comprises manipulating an egg in order to force an intermediate layer between the outer egg shell and the interior of the egg, towards the sample passage. The intermediate layer may support in closing off the sample passage, thus even more preventing ingress of pollution into the interior of the egg.

In an embodiment, the method comprises maintaining the egg in a predetermined position during a settling time before expelling the amount of fluid from the interior of the egg to the exterior of the egg. This makes the location of the sample position more predictable and facilitates the expelling of the amount of fluid since fluid has accumulated.

The invention also provides an egg sampling device configured to execute the method according to a preceding claim.

The invention further relates to a device comprising one or more of the characterising features described in the description and/or shown in the attached drawings.

The invention further relates to a method comprising one or more of the characterising features described in the description and/or shown in the attached drawings.

Modifications and alternative implementations of some parts or elements are possible, and are included in the scope of protection as defined in the appended claims.

The various aspects discussed in this patent can be combined in order to provide additional advantages.

DESCRIPTION OF THE DRAWINGS

The invention will be further elucidated referring to the schematic drawings wherein shown in.

DETAILED DESCRIPTION OF EMBODIMENTS

FIG. 1A-E show embodiments of the method for sampling an egg according to the invention.

Figure 1A:
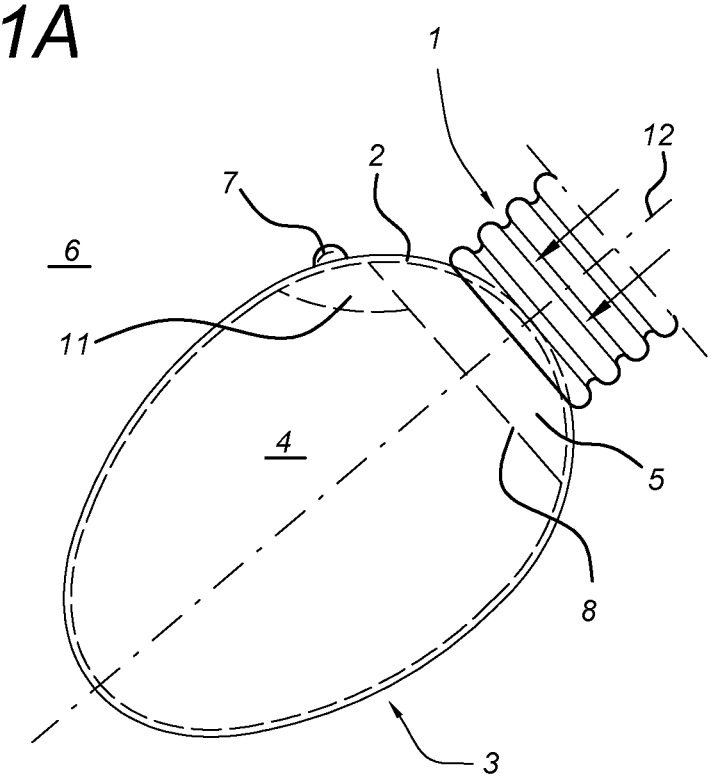
FIG. 1A-G in side view a number of embodiments of the method for sampling an egg according to the invention.

FIG. 1A shows a cup 1 that is designed to fluid couple with the shell 2 of an egg 3. The cup 1 is fluid coupled with a source of pressure (not shown here). As a result, an interior 4 of the egg 3 is fluid coupled to the source of pressure through the cup 1 and because of the porosity of egg shell 2. An egg shell 2 has pores (not shown) for gas exchange between the interior 4 of an egg 3 and the exterior 6. These pores have a diameter between 1 to 10 microns.

As soon as the interior 4 of the egg 3 is fluid coupled to the source of pressure, the pressure in the interior 4 of the egg 3 can be controlled by the source of pressure. The amount of fluid 7 is expelled from the interior 4 of the egg 3 to the exterior 6 of the egg 3 as a result of overpressure applied to the cup 1. In other words, the cup 1 is pushed on the egg 3 and an overpressure is applied to the suction cup 1.

A pressure difference between the interior 4 of an egg 3 and the exterior 6 results in transport of fluid through the egg shell 2. Here, the pressure in the interior 4 exceeds the atmospheric pressure at the exterior 6 and as a result an amount of fluid 7 is expelled from the interior 4 of the egg 3 to the exterior 6 of the egg 3. In this case, the expelled amount of fluid 7 is allantoic fluid.

Downstream in the process of the method, a portion of the amount of fluid 7 is collected at the exterior surface 2 of the egg 3, as is best shown in FIG. 2, 3.

Once the egg is sampled, any desired analyses can be executed with the collected portion of the amount of fluid 7, like determining the gender of the embryo situated in the egg 3.

Method according to a preceding claim, wherein controlling the pressure in the interior of the egg by the source of pressure comprises applying a pressure difference between the interior and the exterior of the egg Method according to claim #, wherein the fluid coupling the interior of the egg to a source of pressure comprises engaging a contact area of the egg shell, preferably a contact area at the air cell FIG. 1B-G show different embodiments of the method for sampling an egg according to the invention. In general, only differences compared with FIG. 1A are described.

Figure 1B:
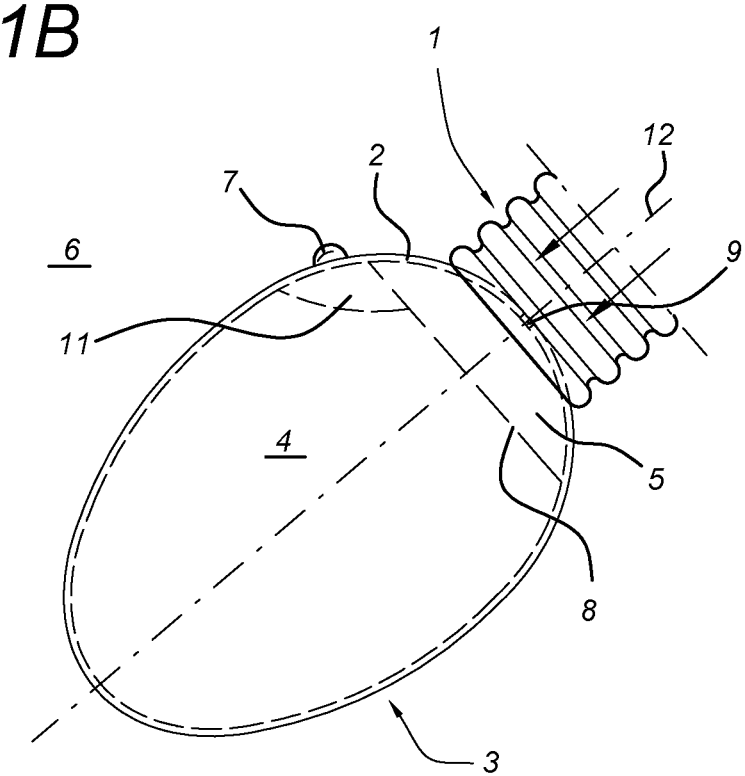

FIG. 1B shows the cup 1 fluid coupled with the shell 2 of an egg 3. In the egg shell a flow path 9 is made by machine action to the egg shell 2. The cup 1 is positioned over the flow path 9 in order to fluid couple the interior 4 of the egg 3 to the source of pressure. The flow path 9 works in parallel to the pores that are present in the egg shell 2. The flow path 9 is made at the air cell 5 of the egg 3. The air cell 5 is a convenient position to breach the protection that the egg shell 2 offers to an embryo in the interior 4 of the egg 3. A reason therefore is a membrane 8 that separates the air cell 5 form the remainder of the interior 4 of the egg 3. The membrane 8 is flexible so therefore, the interior 4 of the egg can be pressurized through the air cell 5.

Figure 1C:
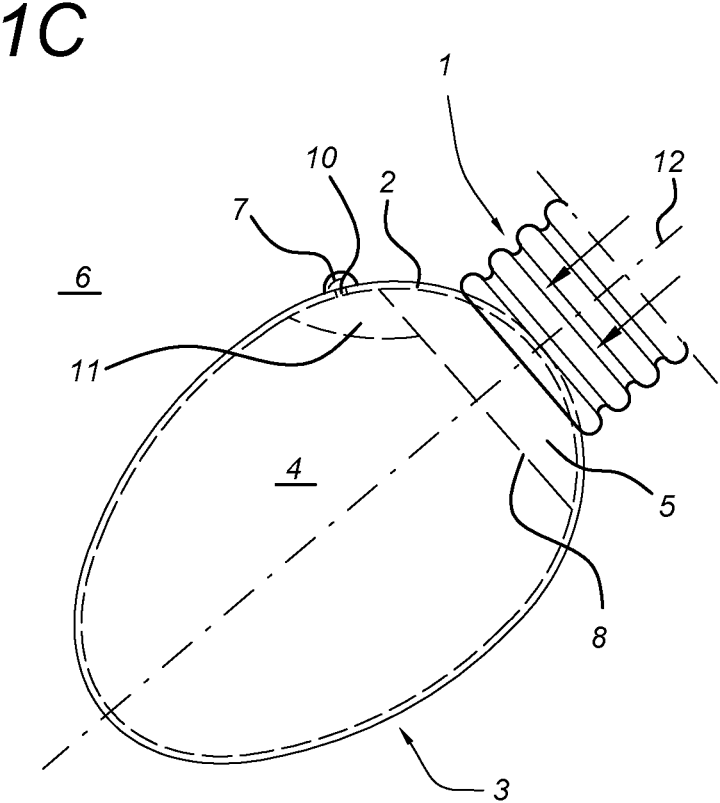

FIG. 1C shows the cup 1 fluid coupled with the shell 2 of an egg 3. In the egg shell a sample passage 10 is made by machine action to the egg shell 2. The sample passage 10 facilitates fluid communication between the interior 4 of the egg 3 and an exterior 6 of the egg 3. The sample passage 10 works in parallel to pores that are present in the egg shell 2. The sample passage 10 may a diameter smaller than 1 mm, in particular smaller than 600 μm which is a big passage compared with pores that have a diameter of 1 to 10 microns. The portion of the amount of fluid 7 is collected at the sample passage 10. The sample passage 10 is provided near the air cell 5 but however past the membrane 8 as seen from the air cell 5. The membrane 8 separates the air cell 5 and the sample passage 10. The sample passage 10 is therefore positioned at the locality where allantoic fluid accumulates.

The sample passage 10 may have a cylindrical shape, however a conical shape that tapers toward the exterior 6 of the egg 3 is conceivable as well.

Where one sample passage is shown, it will be conceivable that a number of passages can be provided. These number of passages can be arranged in a pattern. In case of three or more passages, the pattern may have a triangular shape or circular shape. The number of passages are arranged within a surface of 4 mm$^2$ up to 100 mm$^2$ to facilitate collecting of a portion of the amount of fluid 7.

Figure 1D:
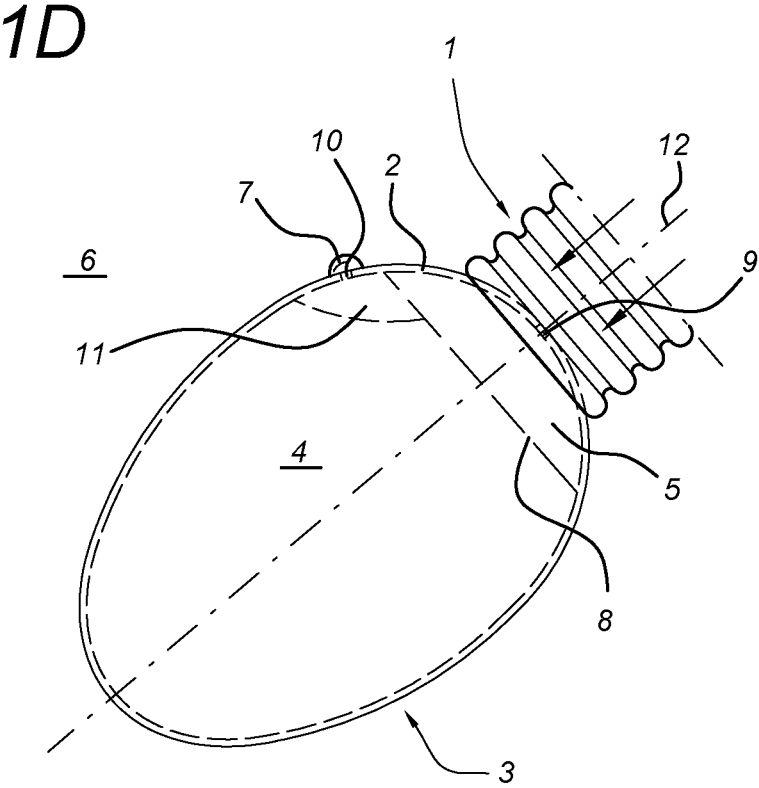

FIG. 1D shows the cup 1 fluid coupled with the shell 2 of an egg 3. In the egg shell 2 a sample passage 10 is made as well as the flow path 9.

Figure 1E:
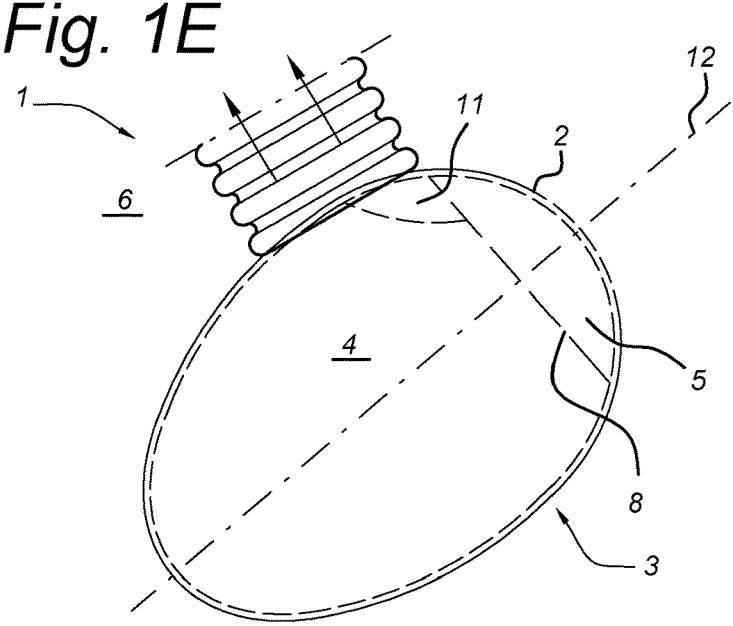

FIG. 1E shows the cup 1 fluid coupled with the shell 2 of an egg 3. The cup 1 is positioned near the air cell 5 but however past the membrane 8. The cup 1 is therefore positioned at the locality where allantoic fluid accumulates. In this case, the expelling the amount of fluid 7 from the interior 4 of the egg 3 to the exterior 6 of the egg 3 as a result of underpressure applied to the cup 1. In other words, the cup 1 operates as a suction cup 1. The amount of fluid 7 is expelled within the inner of the cup 1. Although not shown, it will be clear that in this case the sample passage 10 can be made in the egg shell 2 as well if desired.

Figure 1F:
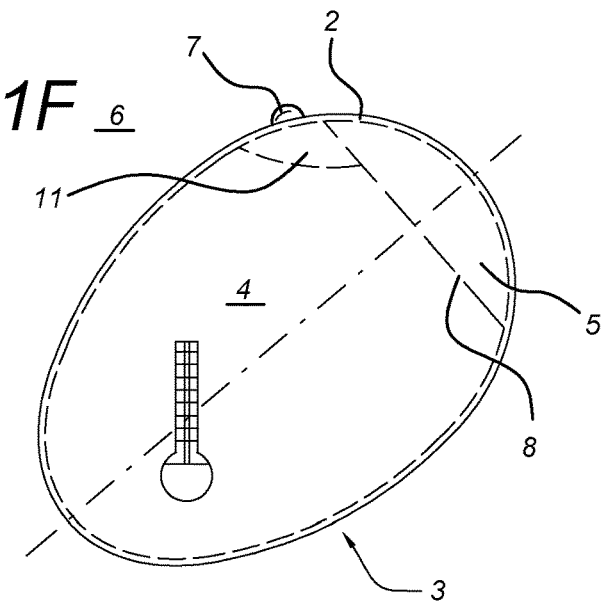

FIG. 1F is similar to FIG. 1A or 1E. In this case, the expelling the amount of fluid 7 from the interior 4 of the egg 3 to the exterior 6 of the egg 3 is caused by a temperature increase of the egg 3 that is shown with a temper. The temperature of the interior 4 of the egg 3 can be increased by any suitable means like based on microwave action. In addition, the cup 1 can be applied to the egg 3 as well to close off the pores in the egg shell at the air cell and/or to facilitate the expelling the amount of fluid 7 from the interior 4 of the egg 3 to the exterior 6 of the egg 3.

Figure 1G:
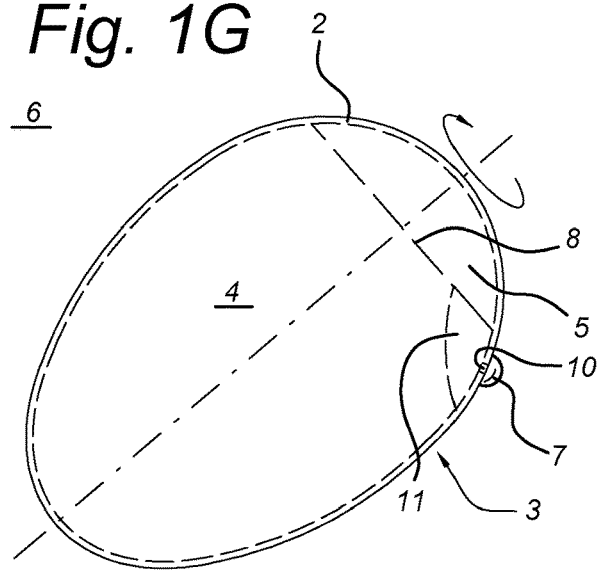

FIG. 1G is similar to FIG. 1C. The egg 3 is rotated along its longitudinal axis 12. In this case, the egg 3 is rotated over about 180° however any angular position will do as long as gravity helps to expel allantoic fluid through the sample passage 10. As a result the sample passage 10 faces downwards. This facilitates fluid communication between the interior 4 of the egg 3 and an exterior 6 of the egg 3. The reason therefor is that the egg content helps to expel allantoic fluid through the sample passage 10 because of gravity. Thus, firstly the allantoic fluid accumulates during a settling time wherein the egg is maintained in a predetermined position shown fin FIG. 1A. Then, the egg is rotated as shown and the amount of fluid 7 is expelled from the interior 4 of the egg 3 to the exterior 6 of the egg 3.

FIG. 2A, 2B, 3A, 3B show a detail of an egg 3 and examples of fluid intake members 13, 14 that collect a portion 15 of the amount of fluid 7.

Figure 2A:
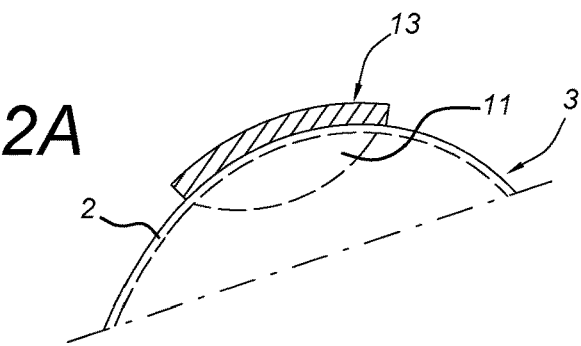
FIG. 2A, 2B, 3A, 3B show a detail of an egg and examples of fluid intake members that collect an amount of fluid.
Figure 2B:
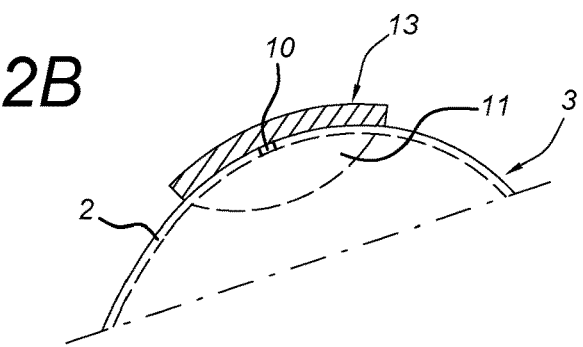

In FIGS. 2A and 2B a fluid intake member 13 is in the form of a tissue paper that functions as an absorbing organ. The fluid intake member 13 is attached to the egg shell 2 of the egg 3. The fluid intake member 13 can be arranged on the exterior of the egg 3 at least before the end of the incubation and be used during incubation. The fluid intake member 13 can be arranged on the exterior of the egg 3 during sampling of the egg 3. The fluid intake member 13 can be arranged on the exterior of the egg 3 at the start of the incubation and be used during incubation. As an option, the fluid intake member 13 can be removed before hatching. The fluid intake member 13 is attached to the egg 3 past the membrane 8 as seen from the air cell 5. In this case, the fluid intake member 13 is attached to the egg 3 near the air cell 5 past the membrane 8. The shown position of the fluid intake member 13 near the air cell 5 is also referred to as the sample position. The fluid intake member 13 is therefore positioned at the locality where allantoic fluid 11 accumulates in the egg 3. A portion or all of the amount of fluid 7 is collected with the fluid intake member 13 by absorption. FIG. 2B differs with FIG. 2A in that a sample passage 10 is provided in the egg shell 2. The fluid intake member 13 cover the sample passage 10. In this case, the fluid intake member 13 covers the entire sample passage 10.

Figure 3A:
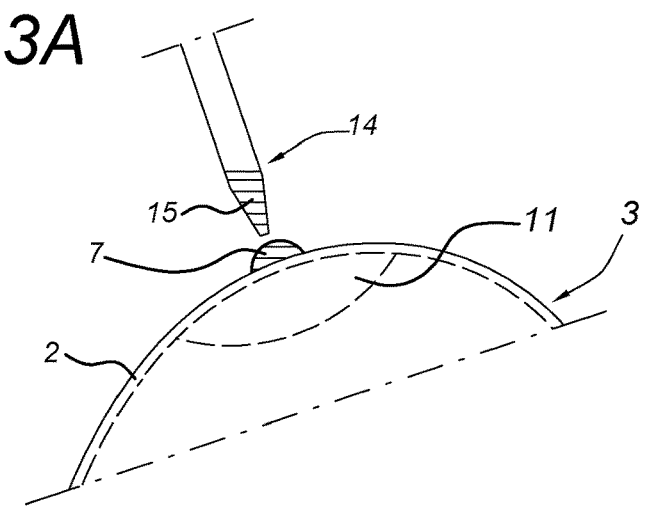
Figure 3B:
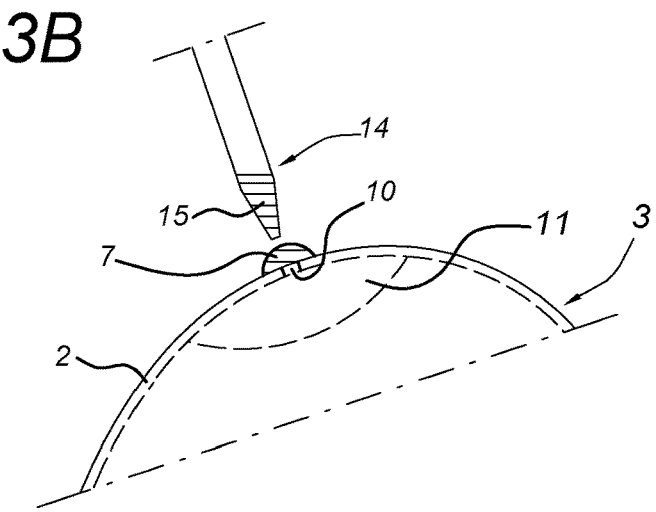

In FIGS. 3A and 3B a fluid intake member 14 is in the form of a capillary tube. The fluid intake member 14 is attached to the egg shell 2 of the egg 3. The fluid intake member 14 approaches to the egg 3 near the air cell 5 but however past the membrane 8. The shown position of the fluid intake member 14 near the air cell 5 is also referred to as the sample position. The fluid intake member 14 is therefore positioned at the locality where allantoic fluid 11 accumulates in the egg 3. FIG. 3B differs with FIG. 3A in that a sample passage 10 is provided in the egg shell 2. A portion 15 of the amount of fluid 7 is collected with the fluid intake member 14 by capillary action.

Figure 4A:
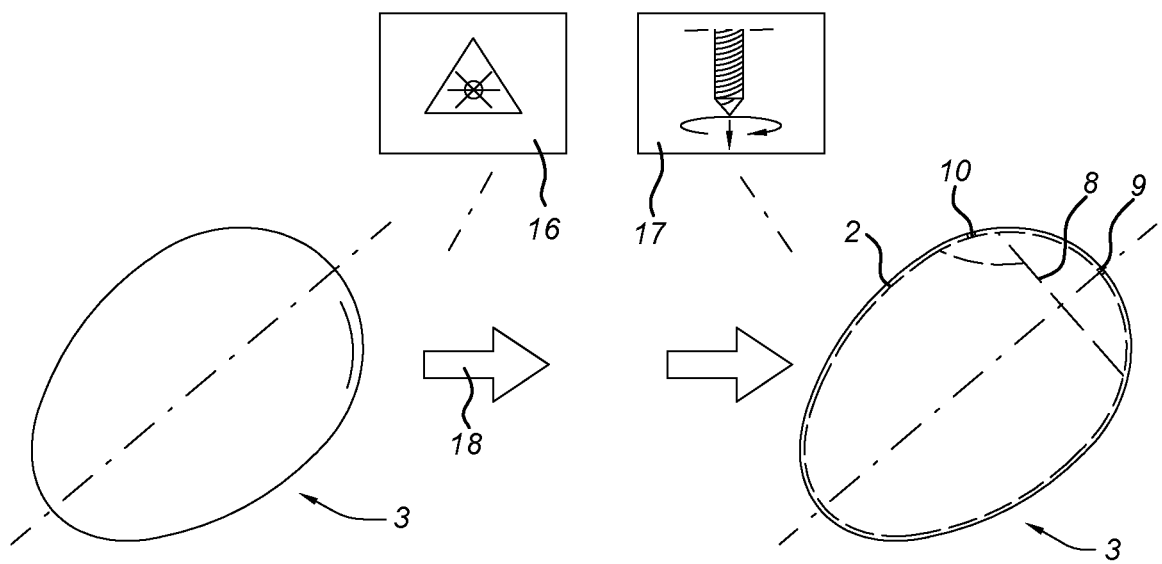
FIG. 4A in side view processing steps for making a sample passage in the egg shell.

FIG. 4A shows in side view processing steps for making a sample passage 10 in the egg shell 2. Making the sample passage 10 comprises laser processing in a laser processing unit 16, and/or processing in a machining unit 17 like a puncturing, cutting, milling or drilling unit. The egg 3 is transported in a process flow direction 18 along the laser processing unit 16, and/or processing in a machining unit 17. It will be clear that the processing steps may also apply to the making of the flow path 9. As an option, the making the sample passage 10 may comprise disinfecting the egg shell proximate the sample passage 10. The disinfecting may comprise laser processing the egg shell 2 proximate the sample passage 10 using the laser processing unit 16.

When making a sample passage 10 and/or making a flow path 9, it is possible that an outer egg shell 2 and intermediate layers need to be crossed. It is conceivable that the outer egg shell 2 and intermediate layers, like for example and if required the membrane 8, are processed with different processing steps.

Figure 4B:
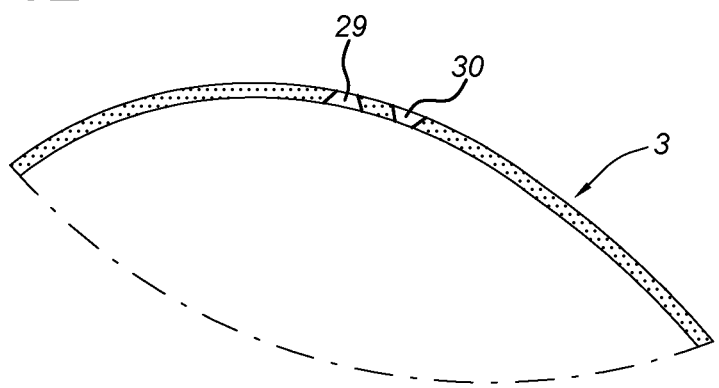
FIG. 4B shows a detail of an egg after the processing step of steps of FIG. 4A.

FIG. 4B shows a detail of an egg 3 after the processing steps for making a sample passage 10 in the egg shell 2. Two possible configurations of tapered sample passages 29. 30 are shown in cross sectional side view. The sample passage 29 tapers out towards the interior 4 of the egg 3. This minimize the area of the sample passage 29 at the outer surface of the egg shell 2 which prevents ingress of pollution. In addition, the sample passage 29 is not easily obstructed by the shell membrane (not shown) that may shift a little with respect to the shell 2. The configuration of passage 29 is in particular enabled by the laser processing unit 16.

The sample passage 30 tapers inward towards the interior 4 of the egg 3. This minimize the area of the sample passage 29 at the inner surface of the egg shell 2 which reduces the risk to damage the content of the egg 3 like important blood vessels.

Figure 5A:
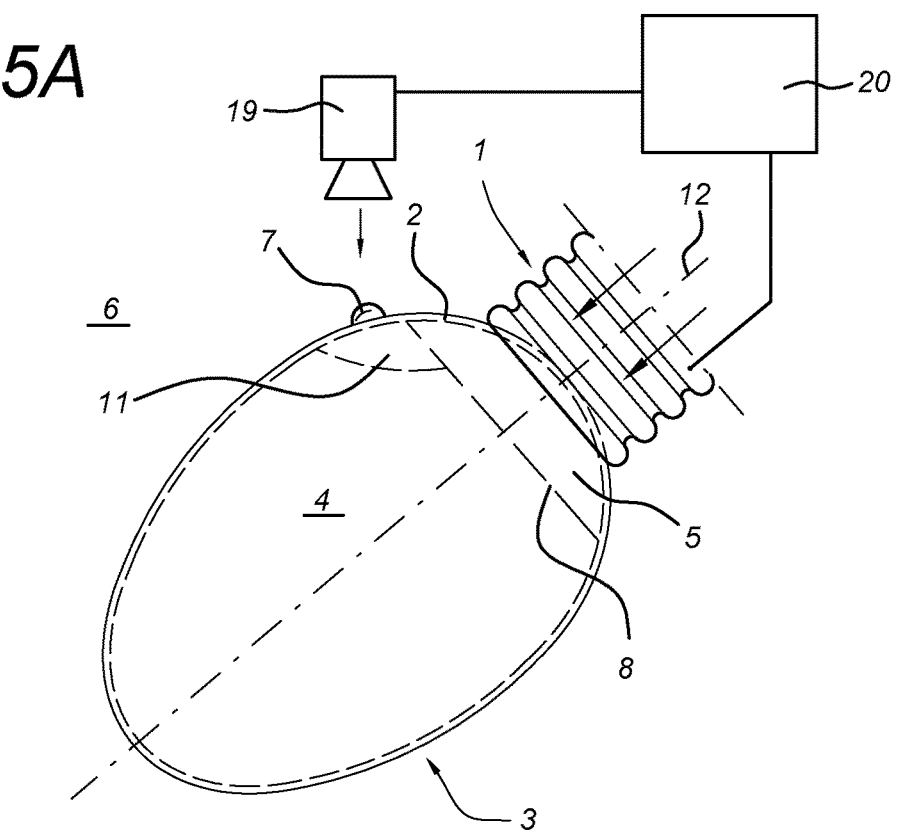
FIG. 5A, 5B show embodiments of a step of sensing an egg.
Figure 5B:
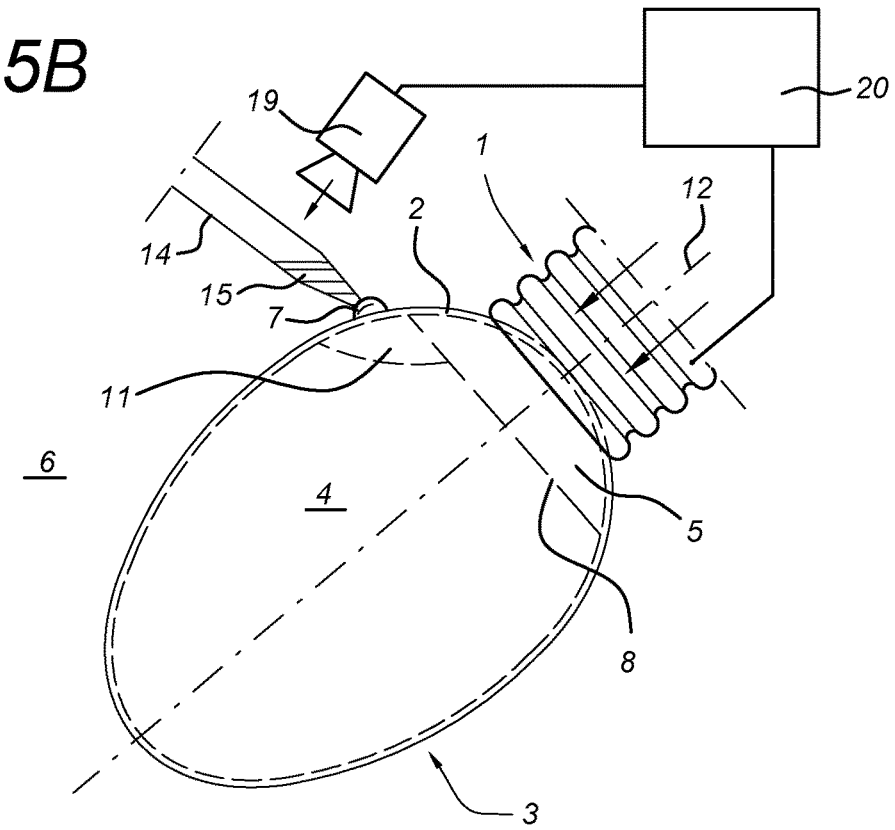

FIG. 5A, 5B show embodiments of a step of sensing the egg 3. A sensor unit 19 is provided to sense the egg 3. The sensor unit 19 is configured to survey an egg and/or for monitoring the amount of expelled sample fluid. The sensor unit 19 may comprise any suitable sensing means like an image capturing device such as a camera. The sensor unit 19 is operationally coupled with a source of pressure 20, in this case a controllable source of pressure 20.

In an egg surveying mode, the following steps are executed; determining a sampling position at the exterior surface 2 of the egg 3; and collecting the portion of the amount of fluid at the sampling position. The sensor unit 19 maps the egg 3 for items like allantoic fluid, the embryo, blood vessels etc. The sampling position is then based on egg sensor data and is normally proximate accumulated allantoic fluid in the egg 3.

In a sample passage making mode, the following steps are executed; sensing at least a portion of the egg 3 to obtain sensor data and making the sample passage 10 depending on the sensor data, in particular determine a position of the sample passage depending on the sensor data. Here, sensing the egg 3 may comprise imaging at least a portion of the egg 3 and measuring a position of the egg 3.

In a sample monitoring mode, the following steps are executed; monitoring the amount of expelled sample fluid 7 to obtain sample fluid amount data and comparing the fluid amount data with a defined minimum amount data and depending on the step of comparing, repeating or maintaining expelling allantoic fluid from the interior 4 of the egg 3 to the exterior 6 of the egg 3 as a result of the pressure in the interior 4 of the egg 4. If enough amount of fluid is expelled, the sample passage 10 can be closed to stop fluid communication through the sample passage 10. In the sample monitoring mode, the sensor unit 19 can be orientated towards the capillary tube 14 in order to directly monitor the portion 15 of the amount of fluid 7 in the capillary tube 14.

FIG. 6A-D show different examples of pressure versus time graphs of pressure in the interior of the egg 3. In all graphs, the atmospheric pressure is referred to with reference number 21. All FIG. 6A-D show that the pressure difference is variable over time.

Figure 6A:
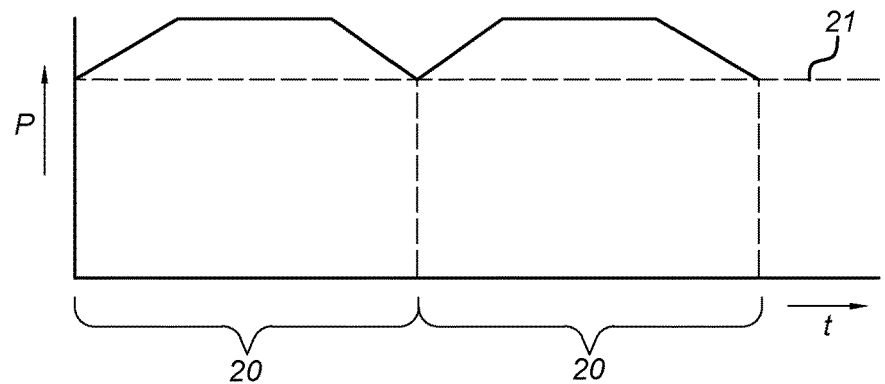
FIG. 6A-D show different examples of pressure versus time graphs of pressure in the interior of the egg.

FIG. 6A shows two subsequent periods 20 of over pressure in the interior 4 of the egg 3.

Figure 6B:
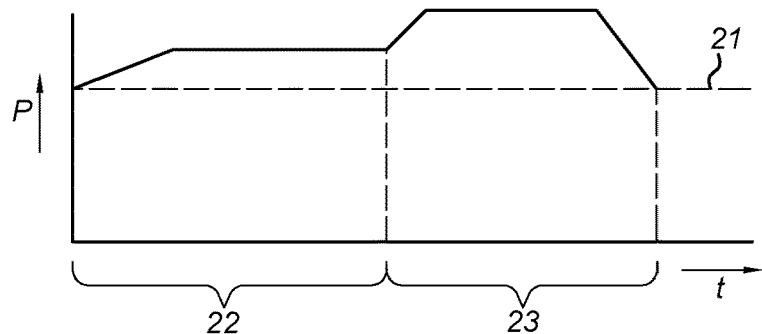

FIG. 6B shows two subsequent periods 22, 23 of over pressure in the interior 4 of the egg 3. The pressure is increased in the second period of time 23 compared with the first period of time 22. FIG. 6B is an example of pressurizing the interior 4 of the egg 3 at an overpressure for as long as the sample passage 10 is open for fluid communication between the interior 4 of the egg 3 and the exterior 6 of the egg 3. Once the sample passage 10 is closed, the pressure can be released to the atmospheric pressure.

Figure 6C:
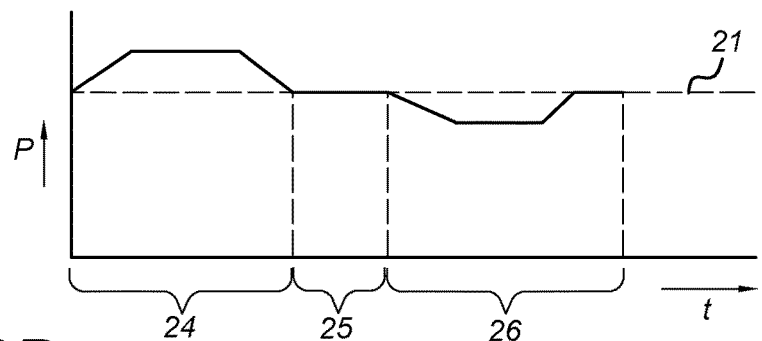

FIG. 6C shows consecutive an active period 24 where over pressure is applied, a neutral period 25 wherein a neutral pressure is applied, and another active period 26 where under pressure is applied to the interior of the egg. The neutral pressure is normally atmospheric pressure that prevails at the exterior 6 of the egg 3.

Figure 6D:
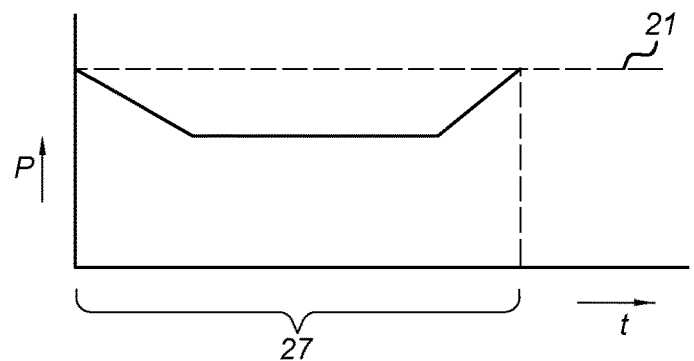

FIG. 6D shows a period 27 of under pressure in the cup 1 that can be applied to the sample passage 10.

Figure 7A:
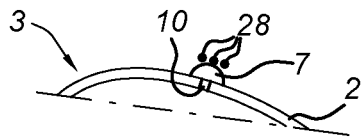
FIGS. 7A and 7B show an embodiment of a process of closing the sample passage.
Figure 7B:
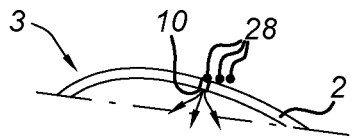

FIGS. 7A and 7B show an embodiment of a process of closing the sample passage 10. The sample passage 10 is closed after expelling the amount of fluid 7 from the interior 4 of the egg 3 to the exterior 6 of the egg 3 as a result of pressure difference. The closing the sample passage 10 stops fluid communication between the interior 4 of the egg 3 and the exterior 6 of the egg 3. The sample passage 10 is closed to prevent ingress of pollution through the sample passage 10. Closing the sample passage 10 comprises contacting the sample passage 10 with a closure element 28. The closure element 28 is here a micro bead 28. A number of micro beads 28 are disposed on the amount of fluid 7. When the amount of fluid 7 is withdrawn back into the interior 4 of the egg 3, the beads 10 are taken with the amount of fluid 7 towards the sample passage 10. At least one micro bead 28 will close off the sample passage 10. The micro bead 10 is configured to close off a sample passage 10. The amount of fluid 7 can be withdrawn back into the interior 4 of the egg 3 by applying a suitable pressure difference. For example, an under pressure can be applied to the interior 4 of the egg 3 or an over pressure can be applied at the sample passage 10. The pressure difference between the interior 4 and the exterior 6 of the egg 3 increases closing contact between the micro bead 28 and the sample passage 10.

Figure 8:
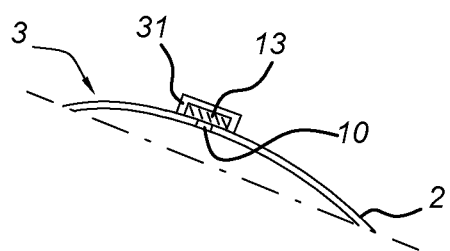
FIG. 8 shows another embodiment of a process of closing the sample passage.

FIG. 8 shows another embodiment of a process of closing the sample passage 10. Closing the sample passage 10 comprises contacting the sample passage 10 with a closure element 28. The closure element 31 is here an adhesive member, in this case a sticker 31. The sticker 31 covers the sample passage 10 and is in sealing contact with the egg shell 2 around the sample passage. As an option, the fluid intake members 13 is integrated with the sticker 31. The sticker 31 may be transparent, or at least have a transparent portion to enable line of sight to the fluid intake member 13.

Figure 9A:
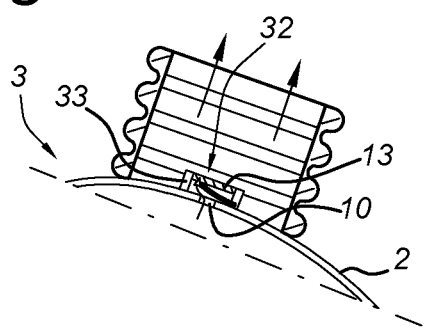
FIGS. 9A and 9B show a further embodiment of a process of closing the sample passage.
Figure 9B:
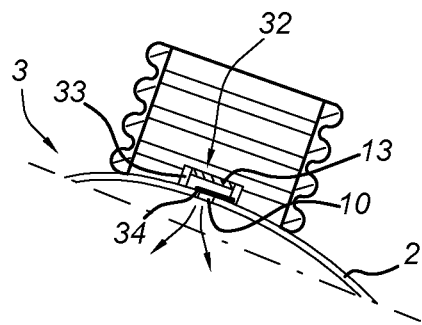

FIGS. 9A and 9B show a further embodiment of a process of closing the sample passage 10. The closure element 34 is here a valve member 34. The valve member 34 is moveable between a sample passage open position shown in FIG. 9A and a sample passage closing position in shown in FIG. 9B. The valve member 24 is preferably a normally closed type of valve member. The valve member 34 is part of a valve device 32. The valve device 32 has a valve support 33. The valve support 33 couples with the egg shell 2. The valve support 33 maintains the valve member 34 at the sample passage 10. The valve member 34 is moveably coupled with the valve support 33. Here, the valve member 34 is moveably coupled with the valve support 33 through a living hinge construction. The valve member 34 is like the micro bead 28, operated by pressure difference. The pressure difference between the interior 4 and the exterior 6 of the egg 3 increases closing contact between the valve member 34 and the sample passage 10. As an option, the fluid intake members 13 is integrated with the valve device 32.

Figure 10A:
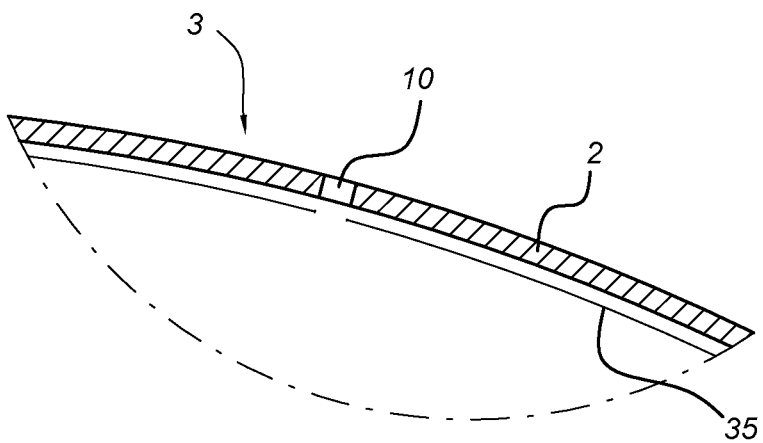
FIGS. 10A and 10B show an even further embodiment of a process of closing the sample passage 10.
Figure 10B:
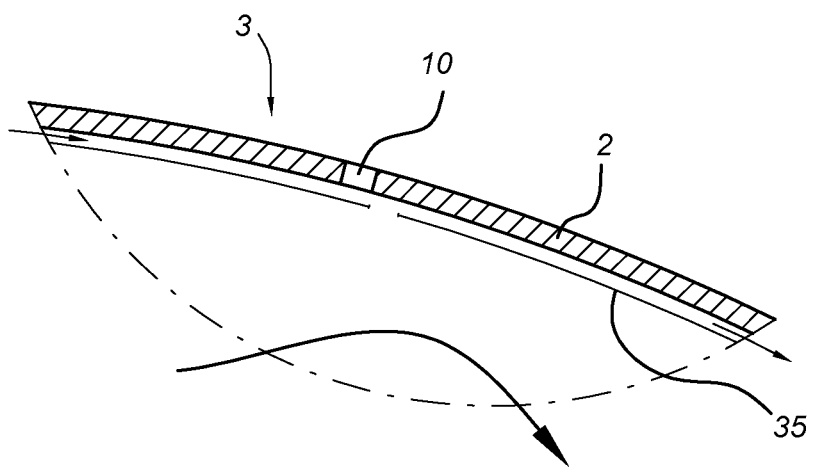

FIGS. 10A and 10B show an even further embodiment of a process of closing the sample passage 10. Here, the closing of the sample passage 10 comprises manipulating an egg in order to force an intermediate layer 35 between the outer egg shell 2 and the interior of the egg, towards the sample passage 10. Manipulating of the egg 3 may include moving, shaking, twisting etc., to make the egg contents move with respect to the egg shell 2. The intermediate layer 35 is the egg shell membrane that closes off the sample passage 10 as shown in FIG. 10 B.

The invention claimed is:

1. A method for sampling an egg, the method comprising;
   a) fluid coupling an interior of the egg to a source of pressure,
   b) controlling the pressure in the interior of the egg by the source of pressure,
   c) expelling an amount of liquid, in particular allantoic liquid, from the interior of the egg to the exterior of the egg as a result of the pressure in the interior of the egg, and
   d) collecting at least a portion of the amount of liquid at the exterior surface of the egg, and
   wherein the method further comprises making a sample passage in an egg shell for fluid communication between an interior of the egg and an exterior of the egg; and step d) comprises collecting the portion of the amount of liquid at the sample passage.

2. The method according to claim 1, wherein the method further comprises determining a sampling position at the exterior surface of the egg; and step d) comprises collecting the portion of the amount of fluid at the sampling position.

3. The method according to claim 1, wherein the sample passage has a dimension smaller than 1 mm, in particular smaller than 600 pm.

4. The method according to claim 1, wherein the making a sample passage in an egg shell for fluid communication between an interior of the egg and an exterior of the egg comprises providing a number of passages, wherein the number of passages are preferably arranged in a pattern having a triangular or circular shape, and wherein preferably the number of passages are arranged within a surface of 4 mm$^2$ up to 100 mm$^2$.

5. The method according to claim 1, wherein making the sample passage comprises disinfecting the egg shell proximate the sample passage, wherein preferably the disinfecting comprises laser processing the egg shell proximate the sample passage.

6. The method according to claim 1, wherein fluid coupling an interior of the egg to a source of pressure comprises coupling the source of pressure to an air cell of the egg.

7. The method according to claim 1, wherein fluid coupling an interior of the egg to a source of pressure comprises making a flow path through the eggs shell to provide a pressure connection between the source of pressure and the interior of the egg.

8. The method according to claim 1, wherein making a sample passage and/or making a flow path comprises processing an outer egg shell and intermediate layers between the outer egg shell and an interior of the egg with different processing steps.

9. The method according to claim 1, wherein the pressure difference is variable over time and preferably the pressure difference is set at a neutral pressure for a neutral period of time and at an active pressure for an active period of time.

10. The method according to claim 1, wherein the fluid coupling the interior of the egg to a source of pressure comprises engaging a contact area of the egg shell, preferably a contact area at the air cell.

11. The method according to claim 1, the method further comprising sensing at least a portion of the egg to obtain sensor data and making the sample passage depending on the sensor data, in particular determine a position of the sample passage depending on the sensor date, wherein sensing the egg comprises at least one or more of imaging at least a portion of the egg and measuring a position of the egg.

12. The method according to claim 1, and further comprising arranging a fluid intake member at the sample position; and step d) comprises collecting the portion of the amount of fluid with the fluid intake member.

13. The method according to claim 12, wherein the fluid intake member is arranged on the exterior of the egg at least before the end of the incubation and is used during incubation.

14. The method according to claim 12, wherein the fluid intake member comprises an absorb organ and the taking in the portion of the amount of fluid is based on capillary action between the absorb organ and the portion of the amount of fluid.

15. The method according to claim 1, comprising pressurizing the interior of the egg for as long as the sample passage is open for fluid communication between the interior of the egg and the exterior of the egg.

16. The method according to claim 1, comprising monitoring the amount of expelled sample fluid to obtain sample fluid amount data and comparing the fluid amount data with a defined minimum amount data and depending on the step of comparing, repeating, intensifying or maintaining at least step c), or closing the sample passage.

17. The method according to claim 1, comprising closing the sample passage to stop fluid communication between the interior of the egg and the exterior of the egg.

18. The method according to claim 17, wherein closing the sample passage comprises contacting the sample passage with a closure element and the method comprises depressurizing the interior of the egg after contacting the sample passage with the closure element in order to increase a closing contact between the closure element and the sample passage.

19. The method according to claim 17, wherein closing the sample passage comprises manipulating an egg in order to force an intermediate layer between the outer egg shell and the interior of the egg, towards the sample passage.

20. The method according to claim 1, comprising maintaining the egg in a predetermined position during a settling time before expelling the amount of fluid from the interior of the egg to the exterior of the egg.

* * * * *